United States Patent
Grasset et al.

(10) Patent No.: US 9,309,167 B2
(45) Date of Patent: *Apr. 12, 2016

(54) PROCESS FOR OLIGOMERIZATION OF OLEFINS THAT USES A CATALYTIC COMPOSITION THAT COMPRISES AN ORGANOMETALLIC COMPLEX THAT CONTAINS AN ALKOXY LIGAND THAT IS FUNCTIONALIZED BY A HETEROATOM

(71) Applicant: IFP ENERGIES NOUVELLES, Rueil-Malmaison Cedex (FR)

(72) Inventors: Fabien Grasset, Bron (FR); Stephane Harry, Jardin (FR); David Proriol, Brignais (FR); Lionel Magna, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 325 days.

This patent is subject to a terminal disclaimer.

(21) Appl. No.: 13/852,403

(22) Filed: Mar. 28, 2013

(65) Prior Publication Data

US 2013/0217941 A1 Aug. 22, 2013

Related U.S. Application Data

(62) Division of application No. 13/109,219, filed on May 17, 2011, now abandoned.

(30) Foreign Application Priority Data

May 18, 2010 (FR) .................................... 10 02090

(51) Int. Cl.
| | |
|---|---|
| C07C 2/34 | (2006.01) |
| B01J 31/02 | (2006.01) |
| C07C 2/32 | (2006.01) |
| C07C 2/36 | (2006.01) |

(52) U.S. Cl.
CPC .............. *C07C 2/34* (2013.01); *B01J 31/0212* (2013.01); *C07C 2/32* (2013.01); *C07C 2/36* (2013.01); *B01J 2231/20* (2013.01); *B01J 2531/46* (2013.01); *B01J 2531/48* (2013.01); *B01J 2531/49* (2013.01); *C07C 2531/14* (2013.01); *C07C 2531/22* (2013.01); *C07C 2531/24* (2013.01); *Y02P 20/52* (2015.11)

(58) Field of Classification Search
CPC ........ C07C 2/34; C07C 2531/24; C07C 2/36; C07C 2531/22; C07C 2531/14; C07C 2/32; B01J 2231/20; B01J 2531/48; B01J 31/0212; B01J 2531/49; B01J 2531/46

USPC .......... 502/102, 113, 117; 585/511, 513, 523, 585/524

See application file for complete search history.

(56) References Cited

U.S. PATENT DOCUMENTS

| | | | |
|---|---|---|---|
| 3,879,485 A | 4/1975 | Belov | |
| 3,911,042 A * | 10/1975 | Belov et al. ................... | 585/512 |
| 4,101,600 A | 7/1978 | Zhukov | |
| 5,292,979 A * | 3/1994 | Chauvin et al. ............... | 585/523 |
| 8,624,042 B2 * | 1/2014 | Grasset et al. ................ | 549/210 |
| 2004/0009349 A1 * | 1/2004 | Brotzman et al. ............ | 428/379 |
| 2007/0135600 A1 | 6/2007 | Otomaru | |

FOREIGN PATENT DOCUMENTS

| | | |
|---|---|---|
| CA | 1 298 829 | 4/1992 |
| FR | 2 341 540 | 9/1977 |
| FR | 2 916 199 | 11/2008 |

OTHER PUBLICATIONS

Langer, A; U.S. Pat. No. 4,434,312: Abstract and structure as shown in SciFinder.*
Flisak, Z.; Szczegot, Z.; Sibelska, I.; Dawidowska-Marynowicz, B; "DFT study of olefin polymerization catalysts based on transition metal complexes with O-donor ligands", Zeszyty Naukowe Politechniki Slaskiej, Chemie, 146, (2001): Abstract and structure as shown in SciFinder.*
Cazaux et al., "Mono(aryloxido) Titanium(IV) Complexes and Their Application in the Selective Dimerization of Ethylene", European Journal of Inorganic Chemistry, 2009(20), 2942-2950. (Jun. 2, 2009).
Jones et al., "Zirconium Complexes as Catalysts for the Oligomerisation of Ethylene: The Role of Chelate Ligands and the Lewis Acid Cocatalyst in the Generation of the Active Species", Journal of Molecular Catalysis A: Chemical 138:37-52 (1999).
Oouchi et al., "Ethylene Oligomerization Catalyzed with Dichlorobis-(beta-Diketonato)Zirconium/Organoaluminium Chloride Systems", Macromol. Chem. Phys., 197:1545-1551. (1996).
Szczegot et al. Abstract cited in SciFinder, 22(11), 399-401, Polimery Warsaw, Poland. (1977).
Search Report of FR 1002090 (Dec. 15, 2010).

* cited by examiner

Primary Examiner — In Suk Bullock
Assistant Examiner — Aaron Pierpont
(74) Attorney, Agent, or Firm — Millen, White, Zelano & Branigan, P.C.

(57) ABSTRACT

The invention describes a process for oligomerization of olefins into compounds or into a mixture of compounds of general formula $C_pH_{2p}$ with $4 \leq p \leq 80$ that employs a catalytic composition that comprises at least one organometallic complex of an element of group IV that is selected from titanium, zirconium, and hafnium, wherein the organometallic complex contains at least one alkoxy-type ligand that is functionalized by a heteroatom selected from nitrogen, oxygen, phosphorus and sulfur, or by an aromatic group.

15 Claims, No Drawings

PROCESS FOR OLIGOMERIZATION OF OLEFINS THAT USES A CATALYTIC COMPOSITION THAT COMPRISES AN ORGANOMETALLIC COMPLEX THAT CONTAINS AN ALKOXY LIGAND THAT IS FUNCTIONALIZED BY A HETEROATOM

This invention relates to the oligomerization of olefins, in particular ethylene. The oligomerization is defined as the transformation of a monomeric unit into a compound or a mixture of compounds of general formula $C_pH_{2p}$ such as $4 \leq p \leq 80$.

One object of the invention is to provide a process for oligomerization of olefins, preferably of ethylene, propylene and butene, and in a preferred manner of ethylene, using a particular catalytic composition.

It is well known that the monoolefins-α, such as ethylene, propylene or butene-1, can be oligomerized with catalytic systems based on transition metals, such as nickel, chromium, titanium, zirconium or other metals, in the presence of a co-catalyst such as a hydrocarbyl aluminum compound, a hydrocarbyl aluminum halide, or an aluminoxane.

Several types of ligands have been described for stabilizing the catalytic radical and orienting the selectivity of the oligomerization reaction.

The U.S. Pat. No. 3,660,519 describes a catalytic composition for oligomerizing the ethylene that limits the proportion of oligomers that are greater than C22. This catalytic composition comprises: (a) a titanium compound of formula $[Ti(OR)_n(Cl)_{4-n}]$ (with n=1 to 4, and with R being an alkyl group that has 1 to 8 carbon atoms); (b) an electron-donor organic compound that contains at least one oxygen or a nitrogen or a phosphorus, (c) a chloro-alkyl aluminum compound, and (d) another organic compound that contains sulfur. The organic additives that are proposed in this composition make it possible to monitor the distribution of the oligomers that are produced by limiting those that are greater than C22.

The U.S. Pat. No. 3,584,071 claims a catalytic composition for the oligomerization of ethylene, comprising diphenyl ether that is combined with titanium tetrachloride and ethyl aluminum sesquichloride to increase the proportion of oligomers from C10 to C18.

In the patent EP 0,722,922 B1, the IPCL Company claims a catalytic composition that comprises a tetraphenoxy titanium compound $Ti(OAr)_4$, in which OAr is a phenoxy group that is ortho-substituted or para-substituted or both by alkyl chains, whereby the activator is an alkyl aluminum and in particular ethyl aluminum sesquichloride, for oligomerizing the ethylene into a mixture of C4 to C36 alpha-olefins. The addition of an organic compound that contains a heteroatom that is based on sulfur, oxygen or phosphorus makes it possible to improve the monitoring of the distribution of olefins.

Other compounds of titanium or zirconium that comprise two alkoxy or aryloxy entities that may or may not be linked to one another are known for catalyzing the polymerization of ethylene in the presence of various activators including methylaluminoxane, whereby the polymerization of ethylene implements a number of patterns of greater than 100 in a manner that is known to one skilled in the art and makes it possible to obtain solid polymers.

The primary drawback of the catalytic systems that are based on titanium or zirconium that involve the alkoxy or phenoxy ligands and lead to the formation of oligomers from ethylene is the formation of polymers in addition to the oligomers, which can also be the cause of a quick deactivation of the catalyst. The monitoring of the distribution of these oligomers is a very significant parameter for the industrial future of this type of catalytic system. In the majority of the systems, this distribution monitoring is associated with the use of additives (organic, etc.), which very often complicates the catalytic composition.

One objective of the invention is to provide a new catalytic composition for the oligomerization of olefins.

Another objective of the invention is to provide a process for oligomerization of olefins that implements said catalytic composition.

Another objective of the invention is, in a preferred embodiment, to provide a process for oligomerization of olefins that, employs a catalytic composition that makes possible a monitoring of the distribution of the oligomers that are obtained. The process for oligomerization of olefins according to the invention makes it possible to obtain a shorter oligomer distribution, in a very preferred manner, of C2 to C14. One advantage of the invention is therefore to provide a selective process for oligomerization of olefins over a range of oligomers.

A process for oligomerization of olefins into compounds or into a mixture of compounds of general formula CpH2p with $4 \leq p \leq 80$ that employs a catalytic composition comprising at least one organometallic complex of an element of group IV that is selected from among titanium, zirconium or hafnium has now been found, whereby said organometallic complex contains at least one alkoxy-type ligand that is functionalized by a heteroatom that is selected from among nitrogen, oxygen, phosphorus or sulfur or by an aromatic group, and has the following for a general formula:

in which:

M is an element from group IV that is selected from among titanium, zirconium, and hafnium, Y is an atom of chlorine or bromine, a hydrocarbyl radical that comprises 1 to 30 carbon atoms, or a radical that is selected from the group that is formed by the alkoxies R'O—, the amidos R'2N—, or the carboxylates R'COO—, where R' is a hydrocarbyl radical that comprises 1 to 30 carbon atoms, n can assume the integer values of 1 to 4, The ligand —OR is an organic compound that is selected from the family of alkoxy ligands whose general structure is as follows:

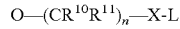

in which:

The functional group L is a group that comprises a heteroatom or an aromatic group, whereby said group that comprises a heteroatom is selected from among the groups —NR$^1$R$^2$, —OR$^3$, —PR$^4$R$^5$, and —SR$^6$, The group X represents a hydrocarbon group (CR$^7$R$^8$), an oxygen atom, or a group that comprises a nitrogen atom —NR$^9$, The groups R$^1$, R$^2$, R$^3$, R$^4$, R$^5$, R$^6$, R$^7$, R$^8$, R$^9$, R$^{10}$, and R$^{11}$ represent a hydrogen atom or a hydrocarbon chain that may or may not be cyclic, comprising 1 to 30 carbon atoms, n can assume the integer values of 0 to 30, and preferably 0 to 10.

Within the scope of the invention, the term "alkoxy" is defined as being a group that corresponds to the general formula —OR, in which the group R is an alkyl or substituted alkyl group. This definition of the term "alkoxy" does not include the groups of aryloxy or phenoxy type. In the catalytic composition according to the invention, the alkoxy-type ligand as defined above is functionalized by a heteroatom that is selected from among nitrogen, oxygen, phosphorus, sulfur, arsenic and antimony or by an aromatic group, and it corresponds to the claimed formulation.

Preferably, M is an element of group IV that is selected from among titanium and zirconium.

Preferably, Y is a radical that is selected from the group that is formed by the alkoxies R'O— where R' is a hydrocarbyl radical, preferably non-functionalized, comprising 1 to 30 carbon atoms. In an also preferred manner, Y is a chlorine atom.

Preferably, the group $(CR^{10}R^{11})_n$ is selected from among the following groups: —CH$_2$—, —(CH$_2$)$_2$—, —(CH$_2$)$_3$—, (CH$_2$)$_4$—, —(CH$_2$)$_5$—, —C(CH$_3$)$_2$—, —C(CH$_3$)$_2$—CH$_2$—, —C(CH$_3$)$_2$—CH$_2$—CH$_2$—, —C(CF$_3$)$_2$—, —C(CF$_3$)$_2$—CH$_2$— and —C(CF$_3$)$_2$—CH$_2$—CH$_2$—.

Preferably, said functional group L is selected from among the following groups: methoxy (—OMe), butoxy (—OBu), dimethylamino (—NMe$_2$), pyrrolidine (C$_4$H$_8$N), pyridino (—C$_5$H$_4$N), phosphino (—PR$_2$), in which R is an alkyl or aryl group that may or may not be substituted, thiofene (—C$_4$H$_3$S), tetrahydrofuran (—C$_4$H$_7$O), furan (—C$_4$H$_3$O), and phenyl (—C$_6$H$_5$), whereby said groups may or may not be substituted. Said group L is preferably the phosphino group (—PR$_2$), in which R is an alkyl or aryl group that may or may not be substituted.

Preferably, X represents a hydrocarbon group $(CR^7R^8)$. In a very preferred manner, X is a hydrocarbon group $(CR^7R^8)$ that is selected from among the groups —CH$_2$— and —C(CH$_3$)$_2$.

The catalytic composition that is used in the oligomerization process according to the invention can advantageously also contain a hydrocarbyl aluminum compound, called an activating agent, selected from the group that is formed by the tris(hydrocarbyl)aluminum compounds, the chlorinated or brominated hydrocarbyl aluminum compounds, and the aluminoxanes.

The tris(hydrocarbyl)aluminum compounds, and the chlorinated or brominated hydrocarbyl aluminum compounds preferably correspond to the general formula AlR"$_x$Z$_{3-x}$ in which R" represents a monovalent hydrocarbon radical that contains, for example, up to 12 carbon atoms, such as alkyl, aryl, aralkyl, alkaryl or cycloalkyl, Z represents a halogen atom that is selected from among, for example, chlorine and bromine, whereby Z is preferably a chlorine atom, and x assumes a value of 1 to 3. As examples of such compounds of formula AlR"$_x$Z$_{3-x}$, it is possible to mention ethyl aluminum sesquichloride (Et$_3$Al$_2$Cl$_3$), dichloroethyl aluminum (EtAlCl$_2$), dichloroisobutyl aluminum (iBuAlCl$_2$), chlorodiethyl aluminum (Et$_2$AlCl), and triethyl aluminum (AlEt$_3$). Among the aluminoxanes that can be used according to the invention, it is possible to cite methyl aluminoxane and modified methyl aluminoxane (MMAO). These activating agents can be used alone or in a mixture.

According to the nature of the organometallic complex [M(OR)$_n$Y$_{(4-n)}$], the activating agent can also be selected from the group of tris(aryl)borane-type Lewis acids, such as tris(perfluorophenyl)borane, tris(3,5-bis(trifluoromethyl) phenyl)borane, tris(2,3,4,6-tetrafluorophenyl)borane, tris (perfluoronaphthyl)borane, tris(perfluorobiphenyl)borane and derivatives thereof. As an activator, it is also possible to use an (aryl)borate combined with a triphenylcarbenium cation or with a trisubstituted ammonium cation, such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl) borate, or triphenylcarbenium tetrakis(3,5-bis (trifluoromethyl)phenyl)borate.

Without being tied by any theory, the functional group L that is characterized by the presence, of a heteroatom that is selected from among nitrogen, oxygen, phosphorus and sulfur or by the presence of an aromatic group is able to interact with the metal center M by forming a connection of, for example, the dative type that thus promotes the formation of the active complex in catalysis and contributes to its stability.

Without being limiting, the examples below illustrate the ligands "O—$(CR^{10}R^{11})_n$—X-L" according to the invention.

The ligands are shown below in their protonated form.

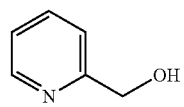

L1

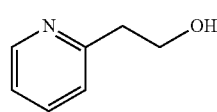

L2

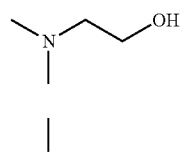

L3

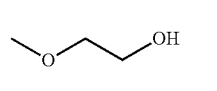

L4

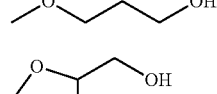

L5

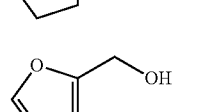

L6

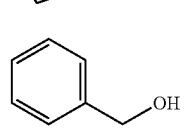

L7

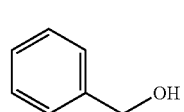

L8

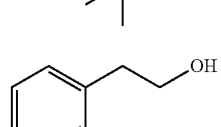

L9

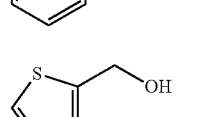

L10

L11

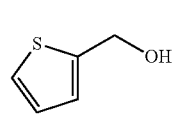

L12

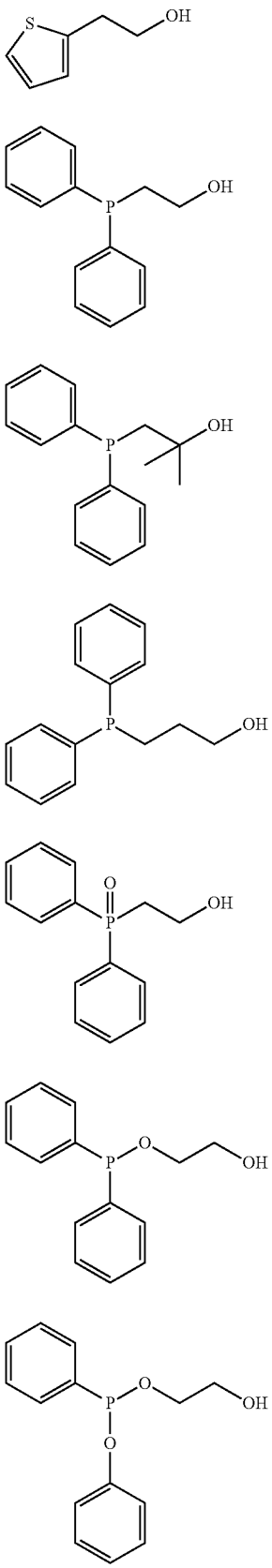
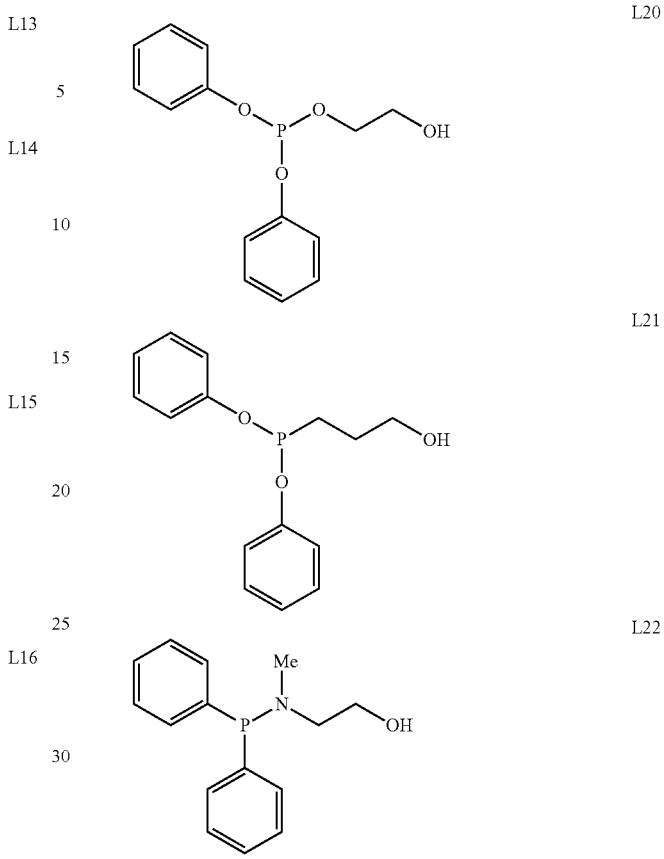

Process for the Preparation of the Organometallic Complex

The process for the preparation of the organometallic complex of an element of group IV that is selected from among titanium, zirconium or hafnium of the catalytic composition that is used in the process according to the invention is done according to the methods that are known in the literature that relate to the synthesis of the organometallic complexes comprising at least one alkoxy ligand. Any process for preparation of this compound may be suitable, such as, for example, the reaction of the alkoxy-type ligand that is functionalized by a heteroatom that is selected from among nitrogen, oxygen, phosphorus or sulfur or by an aromatic group, with a salt of an element of group IV that is selected from among titanium, zirconium or hafnium in an organic solvent, such as, for example, an ether, an alcohol, an alkane such as, for example, pentane, an aromatic solvent such as, for example, toluene, or a chlorinated solvent such as, for example, dichloromethane.

According to a preferred embodiment of said process for preparation, the organometallic complex is prepared in situ in the solvent that is used for the oligomerization reaction. In this case, the mixing order of the salt of the element of group IV that is selected from among titanium, zirconium or hafnium, and the ligand is not critical. However, in a preferred manner, a solution of a compound of the element of group IV that is selected from among titanium, zirconium or hafnium that is soluble in an organic medium is first prepared, and next the alkoxy-type ligand that is functionalized by a heteroatom that is selected from among nitrogen, oxygen, phosphorus or sulfur or by an aromatic group is added.

According to another preferred embodiment of said process for preparation, said organometallic complex is isolated before solubilization in the solvent of the oligomerization reaction.

Process for Preparation of the Catalytic Composition that is Used in the Process According to the Invention.

In the case where the catalytic composition that is used in the oligomerization process according to the invention also comprises an activating agent, the two components of said catalytic composition, i.e., the organometallic complex and the activating agent, are advantageously brought into contact, in any order, in a solvent that is selected from the group that is formed by the aliphatic and cycloaliphatic hydrocarbons, such as hexane, cyclohexane, heptane, butane or isobutane, whereby the unsaturated hydrocarbons such as the monoolefins or diolefins comprise, for example, 4 to 20 carbon atoms, the aromatic hydrocarbons such as benzene, toluene, ortho-xylene, mesitylene, ethylbenzene and the chlorinated hydrocarbons, such as chlorobenzene or dichloromethane, pure or in a mixture. Advantageously, the aliphatic hydrocarbons such as n-heptane and the aromatic hydrocarbons such as ortho-xylene are used.

According to another preferred embodiment of the process for preparation of said catalytic composition and when an activating agent is used, the activating agent is added in a solution that contains the organometallic complex of the element of group IV that is selected from among titanium, zirconium, or hafnium.

The concentration of the element M of group IV that is selected from among titanium, zirconium or hafnium in the catalytic solution is advantageously between $1.10^{-4}$ to 1 mol/L, preferably from $1.10^{-3}$ to 0.5 mol/L.

The molar ratio between the optional activating agent and the organometallic complex of the element M of group IV that is selected from among titanium, zirconium or hafnium is advantageously between 1/1 and 1,800/1, preferably from 2/1 to 800/1, and in a preferred manner between 2/1 and 500/1.

The temperature at which the components of the catalytic system are mixed is advantageously between −10 and +180° C., preferably between 0 and +150° C., for example at a temperature that is close, to ambient temperature (15 to 30° C.). The mixing can be carried out under an atmosphere of ethylene or inert gas.

Oligomerization Reaction.

The process according to the invention is a process for oligomerization of olefins for producing compounds or a mixture of compounds of general formula $C_pH_{2p}$ with 4≤p≤80, preferably with 4≤p≤50, in a preferred manner with 4≤p≤26, and in a more preferred manner with 4≤p≤14, employing the catalytic composition that is described above.

The feedstock that is used in the process for oligomerization according to the invention consists of C2 to C12 alpha-olefins, and preferably the feedstock is selected from among ethylene, propylene, or butene, and in a very preferred manner, the feedstock is ethylene.

According to a preferred embodiment, in the case where the element M of group IV is titanium, the process according to the invention is a process for dimerization of ethylene, and in an even more preferred manner, a process for selective dimerization of ethylene into butene-1.

Preferably, titanium is used as a metal, triethyl aluminum is used as an activating agent, and a molar ratio of activating agent to organometallic complex of between 1 and 5 is used for the dimerization of ethylene.

According to another preferred embodiment, in the case where the element M of group IV is zirconium, the process according to the invention is a process for oligomerization of the ethylene that makes it possible to obtain a distribution of variable compounds, i.e., compounds or a mixture of compounds of general formula $C_pH_{2p}$ with 4≤p≤30.

Preferably, zirconium is used as a metal, ethyl aluminum sesquichloride is used as an activating agent, and a molar ratio of activating agent to organometallic complex of between 6 and 30 is used for the oligomerization of ethylene.

The oligomerization process of the olefins is advantageously carried out under a total pressure of between 0.5 and 15 MPa, preferably 1 to 10 MPa, and at a temperature of between 20 to 180° C., preferably between 40 and 140° C.

According to a preferred embodiment, the catalytic oligomerization reaction is implemented intermittently. A selected volume of the catalytic solution that is constituted as described above is introduced into a reactor that is equipped with the usual stirring devices, heating devices and cooling devices, and then it is pressurized by ethylene to the desired pressure, and the temperature is adjusted to the desired value. The oligomerization reactor is kept at constant pressure by introducing ethylene until the total volume of liquid that is produced represents, for example, 2 to 50 times the volume of the catalytic solution originally introduced. The catalyst is then destroyed by any conventional means known to one skilled in the art, and then it is drawn off, and the products of the reaction and the solvent are separated.

According to another preferred embodiment, the catalytic oligomerization reaction is implemented continuously. The catalytic solution is injected at the same time as ethylene into a reactor that is stirred by standard mechanical means that are known to one skilled in the art or by an outside recirculation, and it is kept at the desired temperature. It is also possible to inject the components of the catalyst separately into the reaction medium. Ethylene is introduced by an intake valve that is controlled at the pressure that keeps the former constant. The reaction mixture is drawn off by means of a valve that is controlled at the liquid level so as to keep the former constant. The catalyst is continuously destroyed by any conventional means that is known to one skilled in the art, and then the products that are obtained from the reaction as well as the solvent are separated, for example by distillation. The ethylene that has not been transformed can be recycled in the reactor. The catalyst residues that are included in a heavy fraction can be incinerated.

Products that are Obtained:

The oligomerization process according to the invention makes possible the production of compounds or a mixture of oligomer compounds of general formula $C_pH_{2p}$ with 4≤p≤80, preferably with 4≤p≤50, in a preferred manner with 4≤p≤26, and in a very preferred manner with 4≤p≤14. The compounds or mixture of oligomer compounds that are thus obtained are generally liquid oligomer compounds.

These compounds or mixture of compounds find a use, for the lower oligomers (C4, C6, C8, C10), as comonomers with ethylene in the manufacturing of linear low-density polyethylene or as a starting product for the manufacturing of lubricating synthesis oils, and for the olefins that have a chain length of C10 to C26 in the manufacturing of plasticizers and detergents.

The following examples illustrate the invention.

EXAMPLE 1

Synthesis of the Complex [(L7)$_2$Ti(OiPr)$_2$]

3.6 g (35 mmol) of ligand L7, 10 ml of dry cyclohexane, as well as 5 g (17.5 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex [(L7)$_2$Ti(OiPr)$_2$] in the form of an orange oil. The yield is almost quantitative. The structure of the complex is confirmed by $^1$H and $^{13}$C NMR analyses.

EXAMPLE 2

Synthesis of the Complex $[(L8)_2Ti(OiPr)_2]$ 3.4 g (35 mmol) of ligand L8, 10 ml of dry cyclohexane, as well as 5.0 g (17.5 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex $[(L8)_2Ti(OiPr)_2]$ in the form of a dark orange oil. The yield is almost quantitative. The structure of the complex is confirmed by $^1$H and $^{13}$C NMR analyses.

EXAMPLE 3

Synthesis of the Complex $[(L9)_2Ti(OiPr)_2]$ 3.8 g (35 mmol) of ligand L9, 10 ml of dry cyclohexane, as well as 5.0 g (17.5 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex $[(L9)_2Ti(OiPr)_2]$ in the form of a colorless oil. The yield is almost quantitative. The structure of the complex is confirmed by $^1$H and $^{13}$C NMR analyses.

EXAMPLE 4

Synthesis of the Complex $[(L11)_2Ti(OiPr)_2]$ 4.3 g (35 mmol) of ligand L33, 10 ml of dry cyclohexane, as well as 5.0 g (17.5 mmol) of [Ti(OiPr)$_4$] are introduced into a Schlenk flask under argon at ambient temperature. This mixture is next brought to reflux for 30 minutes, and then stirred, still under argon, for one night. The evaporation of the solvent leads to the complex $[(L11)_2Ti(OiPr)_2]$ in the form of an orange oil. The yield is almost quantitative. The structure of the complex is confirmed by $^1$H and $^{13}$C NMR analyses.

EXAMPLE 5

Synthesis of the Complex $[(L12)_2Ti(OiPr)_2]$ 4.0 g (35 mmol) of ligand L12, 10 ml of dry cyclohexane, as well as 5.0 g (17.5 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex $[(L12)_2Ti(OiPr)_2]$ in the form of a yellow liquid. The yield is almost quantitative. The structure of the complex is confirmed by $^1$H and $^{13}$C NMR analyses.

EXAMPLE 6

Synthesis of the Complex $[(L14)_2Ti(OiPr)_2]$ 3.2 g (14 mmol) of ligand L14, 10 ml of dry cyclohexane, as well as 2.0 g (7 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex $[(L14)_2Ti(OiPr)_2]$ in the form of a yellow viscous liquid. The yield is almost quantitative. The structure of the complex is confirmed by $^1$H, $^{13}$C and $^{31}$P NMR analyses.

EXAMPLE 7

Synthesis of the Complex $[(L16)_2Ti(OiPr)_2]$ 3.4 g (14 mmol) of ligand L16, 10 ml of dry cyclohexane, as well as 2.0 g (7 mmol) of [Ti(OiPr)$_4$] are introduced into a Schlenk flask under argon at ambient temperature. This mixture is next brought to reflux for 30 minutes and then stirred, still under argon, for one night. The evaporation of the solvent leads to the complex $[(L16)_2Ti(OiPr)_2]$ in the form of a yellow viscous liquid. The yield is almost quantitative. The structure of the complex is confirmed by $^1$H, $^{13}$C, and $^{31}$P NMR analyses.

EXAMPLE 8

Synthesis of the Complex $[(L16)_2Ti(OnBu)_2]$ 2.9 g (12 mmol) of ligand L16, 10 ml of dry cyclohexane, as well as 2.0 g (6 mmol) of [Ti(OnBu)$_4$] are introduced into a Schlenk flask under argon at ambient temperature. This mixture is next brought to reflux for 30 minutes and then stirred, still under argon, for one night. The evaporation of the solvent leads to the complex $[(L16)_2Ti(OnBu)_2]$ in the form of a yellow viscous liquid. The yield is almost quantitative. The structure of the complex is confirmed by $^1$H, $^{13}$C, and $^{31}$P NMR analyses and by elementary analysis.

EXAMPLES 9-16 (According to the Invention)

Selective Dimerization of $C_2H_4$ 0.15 mmol of the complex $[(L)_nTi(OiPr)_{4-n}]$ (or $[(L)_nTi(OnBu)_{4-n}]$), previously solubilized in cyclohexane as described in the invention, is introduced in order under argon atmosphere into a stainless steel autoclave with a useful volume of 35 ml, equipped with electric heating and a cooling system by a compressed air vortex, making it possible to regulate the temperature. Next, 0.45 mmol of triethyl aluminum in solution is introduced into cyclohexane, or an Al/Ti molar ratio 3. The total quantity of cyclohexane is 6 ml. Then, ethylene is introduced into the autoclave in such a way as to maintain a constant pressure of 2 MPa. After a reaction time "t," the introduction of ethylene is stopped, and the reactor cools to ambient temperature. The autoclave is next depressurized, and the catalytic system is neutralized by injection of 1 ml of water. A gaseous fraction and a liquid fraction that are analyzed by chromatography are collected. If necessary, a small quantity of polyethylene is also recovered.

Table 1 below repeats in a detailed manner all of the results that are obtained:

TABLE 1

Results of the Tests According to the Invention

| No. | Nature of the Complex | Time (hour) | Productivity (g/gTi/h) | Distribution (% by Weight) C4 (α) | C6 (α) | PE |
|---|---|---|---|---|---|---|
| 9  | [(L7)$_2$Ti(OiPr)$_2$]  | 1    | 600  | 95 (99+)   | 3 (15)  | 2    |
| 10 | [(L9)$_2$Ti(OiPr)$_2$]  | 1    | 700  | 91 (99)    | 7.5 (6) | 0.5  |
| 11 | [(L11)$_2$Ti(OiPr)$_2$] | 1    | 1400 | 94 (99+)   | 5.5 (8) | 0.5  |
| 12 | [(L8)$_2$Ti(OiPr)$_2$]  | 1    | 800  | 94.5 (99+) | 4.5 (9) | 1    |
| 13 | [(L12)$_2$Ti(OiPr)$_2$] | 1    | 500  | 95 (99+)   | 4 (11)  | 1    |
| 14 | [(L14)$_2$Ti(OiPr)$_2$] | 0.43 | 3400 | 94 (99+)   | 6 (12)  | <0.5 |
| 15 | [(L16)$_2$Ti(OiPr)$_2$] | 0.22 | 6600 | 92 (99+)   | 8 (12)  | <0.5 |
| 16 | [(L16)$_2$Ti(OnBu)$_2$] | 0.15 | 9700 | 93 (99+)   | 7 (9)   | <0.5 |

In this table, the productivity is defined as being the ethylene mass ($C_2H_4$) that is consumed per gram of titanium that is introduced initially and per hour.

The C4 distribution is the quantity of olefins having a carbon atom number that is equal to 4 in the total distribution.

(α1) represents the selectivity of linear butene-1 product in the C4 fraction.

Likewise, the C6 distribution is the quantity of olefins having a carbon atom number that is equal to 6 in the total distribution.

(α2) represents the selectivity of linear hexene-1 product in the C6 fraction.

The selectivity of linear butene-1 product in the C4 fraction and the linear hexene-1 product in the C6 fraction is measured by gas phase chromatography according to a method that is known to one skilled in the art.

EXAMPLES 17-20 (For Comparison)

Selective Dimerization of $C_2H_4$ by [Ti(OiPr)$_4$] in the Presence of Organic Additives that are Not in Accordance with the Invention Examples 17-20 of Table 2 were produced under the same conditions as those described in Table 1 (the reaction time is equal to 1 hour). These examples illustrate the negative effect of the organic additives that have heteroatoms but that are not in accordance with the invention (and therefore the advantage of the process according to the invention) on the productivity of [Ti(OiPr)$_4$] in selective dimerization of the ethylene into butene-1.

TABLE 2

Results of the Comparative Tests

| No. | Nature of the Complex | Nature of the Additive | "Additive/Ti" Molar Ratio | Productivity (g/gTi/h) | Distribution (% by Weight) C4 (α) | C6 (α) | PE |
|---|---|---|---|---|---|---|---|
| 17 | [Ti(OiPr)$_4$] | THF     | 2 | 300  | 97 (99$^+$) | 3 (15)   | <0.5 |
| 18 | [Ti(OiPr)$_4$] | Pyridine| 2 | <100 | 99 (99$^+$) | <0.5     | <0.5 |
| 19 | [Ti(OiPr)$_4$] | MeOBu   | 2 | 700  | 95 (99+)    | <5       | <0.5 |
| 20 | [Ti(OiPr)$_4$] | PPh$_3$ | 2 | 1300 | 96 (99+)    | 3.5 (13) | 0.5  |

EXAMPLE 21

Synthesis of the Complex [(L1)$_2$Zr(OiPr)$_2$]

0.22 g (2 mmol) of ligand L1, 10 ml of dry cyclohexane, as well as 0.39 g (2 mmol) of [Zr(OiPr)$_4$(iPrOH)] are introduced into a Schlenk flask under argon at ambient temperature. This mixture is stirred, still under argon, for one night at ambient temperature. The evaporation of the solvent leads to the complex [(L1)$_2$Zr(OiPr)$_2$] in the form of a white solid. The yield is almost quantitative. The structure of the complex is confirmed by $^1$H and $^{13}$C NMR analyses.

EXAMPLE 22

Synthesis of the Complex [(L11)$_2$Zr(OiPr)$_2$]

0.5 g (1.9 mmol) of Zr(OiPr)$_4$ as well as 10 ml of dry toluene are introduced into a Schlenk flask under argon at ambient temperature. Next, 0.46 g (3.8 mmol) of ligand L11 is added. This mixture is stirred, still under argon, for one night at ambient temperature. The evaporation of the solvent leads to the complex [(L11)$_2$Zr(OiPr)$_2$] in the form of a white viscous oil. The yield is almost quantitative.

EXAMPLE 23 (According to the Invention)

Oligomerization of $C_2H_4$ by the Complex [(L1)$_2$Zr(OiPr)$_2$]

0.05 mmol of the complex [(L1)$_2$Zr(OiPr)$_2$], previously solubilized in a toluene/cyclohexane (1/1) mixture as described in the invention, is introduced in order, under argon atmosphere, into a stainless steel autoclave with a useful volume of 35 ml, equipped with electric heating and a cooling system by compressed air vortex, making it possible to regulate the temperature. Next, 0.59 mmol of aluminum sesquichloride in solution is introduced into the cyclohexane, or an Al/Zr molar ratio=12. The total quantity of solvent is 6 ml.

Then, ethylene is introduced into the autoclave in such a way as to maintain a constant pressure of 4 MPa and a temperature of 80° C. After one hour of reaction, the introduction of ethylene is stopped, and the reactor is cooled to ambient temperature. The autoclave is next depressurized, and the catalytic system is neutralized. A liquid fraction is collected, and said fraction is analyzed by chromatography. The quantity of polymer that is formed is less than 30 mg.

| Productivity (g/gZr/h) | C4 (α) | C6 (α) | C8 (α) | C10 (α) | C12 | C14 | C16 | C18 | C20+ | PE |
|---|---|---|---|---|---|---|---|---|---|---|
| 562 | 45 (97) | 27 (98) | 14 (96) | 7 (92) | 3 | 2 | 1 | <0.5 | <0.5 | <0.5 |

EXAMPLE 24 (According to the Invention)

Oligomerization of $C_2H_4$ by the Complex $[(L11)_2Zr(OiPr)_2]$

The protocol that is used is identical to the one that is described in Example 23 except that 0.05 mmol of $[(L11)_2Zr(OiPr)_2]$ is used. After 45 minutes of reaction, the results are as follows:

| Productivity (g/gZr/h) | C4 | C6 | C8 | C10 | C12 | C14 | C16 | C18 | C20+ | PE |
|---|---|---|---|---|---|---|---|---|---|---|
| 3066 | 24 | 21 | 17 | 12 | 9 | 6 | 4 | 3 | 4 | <0.5 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 10/02090, filed May 18, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oligomerization of olefins into compounds or into a mixture of compounds of the formula $C_pH_{2p}$ with $4 \leq p \leq 80$, said process comprising:
oligomerizing an olefin feedstock in the presence of a catalytic composition comprising at least one organometallic complex of an element of group IV selected from titanium, zirconium, and hafnium, wherein said organometallic complex contains at least one alkoxy ligand functionalized by a heteroatom that is selected from nitrogen, oxygen, phosphorus, and sulfur or by an aromatic group, and said organometallic complex is of the following formula:

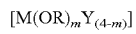

in which:
M is an element from group IV selected from titanium, zirconium, and hafnium,
Y is an atom of chlorine or bromine, a hydrocarbyl radical having 1 to 30 carbon atoms, or a radical selected from alkoxy R'O—, amido R'$_2$N—, and carboxylate R'COO—, where R' is a hydrocarbyl radical having 1 to 30 carbon atoms,
m is an integer of 1 to 4, and
the ligand —OR is an organic compound selected from alkoxy ligands of the formula:

in which:
$(CR^{10}R^{11})_n$ is —$CH_2$—, —$(CH_2)_2$—, —$(CH_2)_3$—, —$(CH_2)_4$—, —$(CH_2)_5$—, —$C(CH_3)_2$—, —$C(CH_3)_2$—$CH_2$—, —$C(CH_3)_2$—$CH_2$—$CH_2$—, —$C(CF_3)_2$—, —$C(CF_3)_2$—$CH_2$— or —$C(CF_3)_2$—$CH_2$—$CH_2$—,
$R^{10}$ and $R^{11}$ each represent a hydrogen atom, —$CH_3$, or —$CF_3$
L is —$PR^4R^5$,
X is a hydrocarbon group $CR^7R^8$, an oxygen atom, or a group that comprises —$NR^9$,
$R^4$ and $R^5$ are each an alkyl or aryl group that is substituted or unsubstituted,
$R^7$, $R^8$, and $R^9$ each represent a hydrogen atom or a hydrocarbon chain, that may or may not be cyclic, having 1 to 30 carbon atoms, and
n is an integer in the range of 1 to 5.

2. The process according to claim 1, wherein said catalytic composition further comprises a hydrocarbyl aluminum activating agent selected from the group consisting of tris(hydrocarbyl)aluminum compounds, chlorinated or brominated hydrocarbyl aluminum compounds, and aluminoxanes.

3. The process according to claim 1, wherein M is titanium or zirconium.

4. The process according to claim 1, wherein Y is an alkoxy R'O—.

5. The process according to claim 1, wherein p is between 4 and 14.

6. The process according to claim 1, wherein the olefin feedstock is ethylene.

7. The process according to claim 3, wherein M is zirconium.

8. The process composition according to claim 3, wherein M is titanium.

9. The process according to claim 1, in which said organometallic complex is $[(L14)_2Ti(OiPr)_2]$, $[(L16)_2Ti(OiPr)_2]$, or $[(L16)_2Ti(OnBu)_2]$, wherein L14 and L16 refer to ligands of formulas L14 and L16, respectively, wherein the ligands are represented in their protonated form

L14

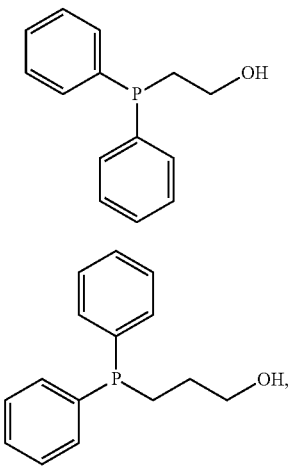

L16 iPr stands for isopropyl, and
nBu stands for n-butyl.

10. The process according to claim 1, wherein m is 2.

11. A process for dimerization of ethylene, said process comprising:
dimerizing ethylene in the presence of a catalytic composition comprising at least one organometallic complex of titanium or zirconium, wherein said organometallic complex contains at least one alkoxy ligand functionalized by a heteroatom that is selected from nitrogen, oxygen, phosphorus, and sulfur or by an aromatic group, and said organometallic complex is of the following formula:

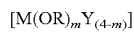

in which:
M is titanium or zirconium,
Y is an atom of chlorine or bromine, a hydrocarbyl radical having 1 to 30 carbon atoms, or a radical selected from alkoxy R'O—, amido R'$_2$N—, and carboxylate R'COO—, where R' is a hydrocarbyl radical having 1 to 30 carbon atoms' is a hydrocarbyl radical having 1 to 30 carbon atoms,
m is an integer of 1 to 4, and
the ligand —OR is an organic compound selected from alkoxy ligands of the formula:

in which:
$(CR^{10}R^{11})_n$ is —CH$_2$—, —(CH$_2$)$_2$—, —(CH$_2$)$_3$—, —(CH$_2$)$_4$—, —(CH$_2$)$_5$—, —C(CH$_3$)$_2$—, —C(CH$_3$)$_2$—CH$_2$—, —C(CH$_3$)$_2$—CH$_2$—CH$_2$—, —C(CF$_3$)$_2$—, —C(CF$_3$)$_2$—CH$_2$, or —C(CH$_3$)$_2$—CH$_2$—CH$_2$—,
L is —PR$^4$R$^5$,
X is a hydrocarbon group CR$^7$R$^8$, an oxygen atom, or a group that comprises —N R$^9$,
R$^4$ and R$^5$ are each an alkyl or aryl group that is substituted or unsubstituted,
R$^7$, R$^8$, and R$^9$ each represent a hydrogen atom or a hydrocarbon chain, that may or may not be cyclic, having 1 to 30 carbon atoms, and
n is an integer in the range of 1 to 5.

12. The process according to claim 11, wherein said process is selective for dimerization of ethylene into 1-butene, wherein M is titanium.

13. The process of claim 11, wherein M is titanium, said catalytic composition further comprises triethyl aluminum, and the molar ratio of triethyl aluminum to said organometallic complex is between 1 and 5.

14. The process of claim 11, wherein M is zirconium, said catalytic composition further comprises ethyl aluminum sesquichloride, and the molar ratio of ethyl aluminum sesquichloride to said organometallic complex is between 6 and 30.

15. The process of claim 13, in which O—(CR$^{10}$R$^{11}$)$_n$—X-L is a ligand of formula L14 or formula L16, wherein the ligands are represented in their protonated form:

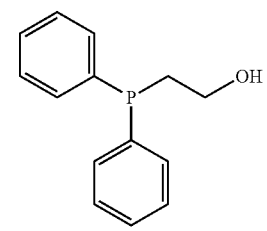

L14

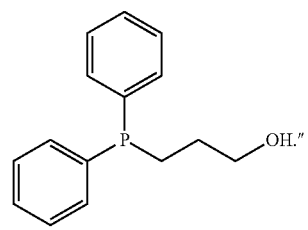

L16

* * * * *